United States Patent [19]

Walker

[11] Patent Number: 5,471,767

[45] Date of Patent: Dec. 5, 1995

[54] BODY WARMING DEVICE

[75] Inventor: Steven H. Walker, Goodlettsville, Tenn.

[73] Assignee: Nu-Stuf, Inc., Lebanon, Tenn.

[21] Appl. No.: 252,884

[22] Filed: Jun. 2, 1994

[51] Int. Cl.$^6$ ................................. A43B 7/02; A61F 7/08
[52] U.S. Cl. ..................... 36/2.6; 36/7.2; 126/204
[58] Field of Search .......................... 219/211, 212, 219/527, 528, 529, 549; 126/204, 206, 207, 208; 607/109, 107, 114, 111; 36/2.6, 7.1 R, 7.2, 7.4

[56] References Cited

U.S. PATENT DOCUMENTS

| | | | |
|---|---|---|---|
| 1,006,415 | 10/1911 | Stubling et al. | |
| 1,355,382 | 10/1920 | Blume. | |
| 2,277,772 | 3/1942 | Marick | 219/46 |
| 2,298,298 | 10/1942 | Joy et al. | 219/46 |
| 2,298,299 | 10/1942 | Joy et al. | 219/46 |
| 2,579,383 | 12/1951 | Goudsmit | 219/46 |
| 2,675,798 | 4/1954 | Rosmarin | 126/204 |
| 2,697,775 | 12/1954 | Licht | 219/46 |
| 2,769,892 | 11/1956 | Collins | 219/46 |
| 2,792,827 | 5/1957 | Gravin et al. | 126/204 |
| 3,249,108 | 5/1966 | Terman | 128/146 |
| 3,487,830 | 1/1970 | Pruett | 36/7.2 X |
| 3,935,856 | 2/1976 | Loftin | 126/208 |
| 4,023,282 | 5/1977 | Ziegelheafer | 36/2.6 |
| 4,042,803 | 8/1977 | Bickford | 219/211 |
| 4,094,080 | 6/1978 | Sanders | 36/2.6 |
| 4,249,319 | 2/1981 | Yoshida | 36/2.6 |
| 4,373,274 | 2/1983 | Michalski | 36/2.6 |
| 4,455,764 | 6/1984 | Rock et al. | 36/136 |
| 4,495,659 | 1/1985 | Madnick et al. | 2/66 |
| 4,949,887 | 8/1990 | Holmes | 224/151 |

*Primary Examiner*—Paul T. Sewell
*Assistant Examiner*—Ted Kavanaugh
*Attorney, Agent, or Firm*—Pitts & Brittian

[57] ABSTRACT

A body warming device (10) for warming a user's feet during sedentary activities and a user's hands during substantially any selected activity. A shell member (26) is provided for covering the selected portion of the user's body to be warmed. A heat source receptacle (14) is provided for receiving and retaining a heat source (16). A closure (18) is provided for selectively closing the heat source receptacle (14) in order to prevent the unselected removal of the heat source (16). Insulation (20) is provided between the shell member (26) and the heat source receptacle (14) for regulating the temperature within the shell member (26). The insulation (20) is non-migratory to maintain an even distribution. A lining member (22) may be incorporated to cover the insulation (20). An edging member (24) may be provided for protecting the edges of the panel members (28), the lining (22), and the insulation (20). A heat source (16) is provided for generating heat within the shell member (26). A sole member (28A) may be included for use with warming feet. A strap member (56) is provided for preventing the body warming device (10) from unselected removal of the user's foot. A tab (58) may be provided for easy engagement of the strap member (56).

10 Claims, 4 Drawing Sheets

BODY WARMING DEVICE

This application in part discloses and claims subject matter disclosed in my earlier filed pending application, Ser. No. 08/050,893 filed on Apr. 21, 1993 now abandoned, which in part discloses and claims subject matter in my earlier filed application, Ser. No. 07/853,253 filed on Mar. 18, 1992, which is now abandoned.

TECHNICAL FIELD

This invention relates to devices used for warming a person's body during sedentary activity. More specifically, the present invention relates to a device which may be worn over the shoes of a user for warming the user's feet during sedentary activities, or which may be used to warm the user's hands during most activities, the device including a heat source which is positioned proximate one of the sympathetic centers of the body's posterior hypothalamus.

BACKGROUND ART

It is well known that the human body is equipped a number of sympathetic centers, or thermostats, which help control its internal temperature. Specifically, the hands, feet, forehead, and ears serve to regulate the body temperature. When one or all of these more highly exposed areas becomes cold, the human body loses internal heat, causing the remainder of the body to become cold.

It is well known that blood flow through the body helps to maintain the proper internal temperature, and when blood flow slows, that temperature declines. Further, it is well known that during sedentary activities such as hunting from a stand or watching outdoor sporting events, the blood flow to the extremities decreases as compared to non-sedentary activities. In cold weather, it is well known that this decrease in blood flow will cause the extremities, especially the feet and hands, to become cold. In extreme weather and extended exposure, the body may suffer sever harm due to frost bite, hypothermia, or other similar physical disabilities.

The body generates heat to the skin by heating blood within the internal organs of the body and pumping the heated blood toward the skin. When the blood flow is decreased, the heat transferred to the skin is proportionally decreased. The blood vessels delivering the heated blood penetrate the subcutaneous insulator tissues and the blood is distributed in the subpapillary portions of the skin.

Immediately beneath the skin is a continuous plexus which is supplied in only the most exposed areas of the body, those being the hands, feet, forehead, and ears. The blood is delivered through direct arteriovenous shunts from the arterioles to the veins. The rate of blood flow to the venous plexus is a determining factor in the conduction of heat from the internal organs to the skin.

The rate of flow to the venous plexus is largely controlled by the vasoconstriction of the arterioles, which is largely controlled by the sympathetic nervous system, the centers of which are those areas being most exposed—the hands, feet, forehead, and ears, as previously described. As the sympathetic centers of the posterior hypothalamus are stimulated, as with the introduction of cold or warm air, the constriction of the arterioles is accordingly increased or decreased, substantially reducing flow of blood to the skin. Cooling the sympathetic centers causes the hypothalamus to constrict the venous plexus, thereby reducing the blood flow, while warming the sympathetic centers causes a dilation of the venous plexus and an increase in blood flow.

Several methods are currently used to help prevent the adverse effects of cold weather. For example, materials have been developed to more efficiently retain the heat produced by the body. These types of materials act as insulation, but serve only to retain heat, and not to produce heat. These materials are used in boots, gloves, and other related articles of clothing for retaining the heat generated by the body proximate the hands and feet.

It is well known that a layer of air surrounding the human body serves as an insulator. The internal body temperature is constantly adjusting to the temperature of the surrounding air such that as the surrounding air cools, the body heat is dissipated. Further, as the body is cooled in this manner, the blood veins in the proximate area constrict, thereby slowing the flow of blood to that area, which also causes a further cooling of the body.

As mentioned, sedentary activity reduces the amount of heat produced by a person's body. The use of insulators to prevent the escape of heat from a person's body during sedentary activity, though helpful, does not serve to maintain the person's body temperature. The insulators merely slow down the decrease of the person's body temperature.

It is desired that a means be provided whereby the body temperature of a user may be elevated by heating the air surrounding a selected body part, thereby avoiding the adverse effects of continued exposure to cold weather during sedentary activities. When used to protect the hands of a user, or other portion of the user's body wherein use of the device will not impair normal functions of that body portion, it is desired that a means may be provided whereby continued use may be carried out whether activity is sedentary or mobile. It is not known to the inventor of the present invention that any such device exists or has been patented.

Other devices have been produced for warming selected portions of the human body. Typical of the art are those devices disclosed in the following U.S. Patents:

| U.S. Pat. No. | Inventor | Issue Date |
| --- | --- | --- |
| 1,006,415 | A. C. Stubling, et al. | Oct 17, 1911 |
| 1,355,382 | A. Blume | Oct 12, 1920 |
| 2,277,772 | L. Marick | Mar 31, 1942 |
| 2,298,298 | M. F. Joy, et al. | Oct 13, 1942 |
| 2,298,299 | M. F. Joy, et al. | Oct 13, 1942 |
| 2,579,383 | F. K. Goudsmit | Dec 12, 1951 |
| 2,675,798 | P. F. Rosmarin | Apr 20, 1954 |
| 2,697,775 | E. H. Licht | Dec 21, 1954 |
| 2,769,892 | D. F. Collins | Nov 6, 1956 |
| 2,792,827 | M. M. Gravin, et al. | May 21, 1957 |
| 3,249,108 | L. A. Terman | May 3, 1966 |
| 3,953,856 | W. M. Loftin | Feb 3, 1976 |
| 4,023,282 | F. Ziegelheafer | May 17, 1977 |
| 4,042,803 | E. P. Bickford | Aug 16, 1977 |
| 4,094,080 | J. J. Sanders | Jun 13, 1978 |
| 4,249,319 | Y. Yoshida | Feb 10, 1981 |
| 4,373,274 | W. J. Michalski | Feb 15, 1983 |
| 4,455,764 | H. E. Rock, et al. | Jun 26, 1984 |
| 4,495,659 | H. Madnick, et al. | Jan 29, 1985 |
| 4,841,646 | L. P. Maurer, Jr. | Jun 27, 1989 |
| 4,949,887 | W. A. Holmes | Aug 21, 1990 |

Of these devices, only those disclosed by Loftin ('856), Ziegelheafer ('282), Maurer, Jr. ('646), Yoshida ('319), Michalski ('274), Sanders ('080), Rock, et al. ('764), and Holmes ('887) are designed to receive a removable heating source and for heating at least a portion of a wearer's foot. Only the Gravin, et al. ('827), Rosmarin ('798) and Holmes ('887) devices disclose a means for receiving a removable heating source for selectively heating a hand of a wearer.

Therefore, only one of the devices disclosed in the above-referenced patents, Holmes ('888), is designed to be used to selectively heat either of the feet or the hands of a wearer. The Holmes device is a multi-use seat cushion which may be use to warm both hands, both feet, the head, a quantity of food, or a seat when used as a seat cushion.

Further, those patents related to the heating of a portion of the wearer's foot do not disclose a device wherein the heat source is disposed proximate the sympathetic center of the foot. Specifically, the heat source is described as being positioned above the toes or at some other location such as under the foot ('319) or at the sides of the foot ('080). The '282 device is also described as being adhered to the boot or shoe of the wearer so as to not be selectively removable from the foot of the wearer without removal of the shoe or boot to which the device is adhered.

None of the prior art devices known to the inventor of the present invention discloses a device wherein a volume is defined for receiving a portion of the wearer's hand or foot, that portion including one of the body's sympathetic centers, wherein the volume is also dimensioned to retain warmed air to prevent loss of heat from the body through that sympathetic center, and wherein the construction includes a heat source receptacle disposed proximate the sympathetic center to be covered. Further, none of the prior art devices known to the present inventor discloses a construction which may be alternately used between the hands and the feet, and specifically to cover at least the upper portion of the top of the user's foot or the back of the user's hand, wherein the construction of the device does not require alteration thereof to move from a hand to a foot, and vice versa.

Therefore, it is an object of this invention to provide a means for warming selected body portions proximate the sympathetic centers—or natural thermostats— of a person during sedentary activity while exposed to cold weather.

Another object of the present invention is to provide a means for maintaining the body temperature generated at the hands and feet of a user.

It is also an object of the present invention to provide such a warming device that may be used to warm other parts of a person's body during any activity while exposed to cold weather.

Another object of the present invention is to provide such a heating device wherein a heat source may be incorporated, the heat source meeting safety standards in order to prevent accidental burns.

Still another object of the present invention is to provide a heating device wherein the heat source may be removed and replaced, thus further providing for the safe cleaning of the warming device.

Yet another object of the present invention is to provide a means for containing a heat source, the means being selectively engageable by one of a person's hands or feet in a manner such that the heat source is positioned proximate one the person's sympathetic centers in order to heat the air surrounding the selected thermostat to prevent the loss of body heat through that center.

DISCLOSURE OF THE INVENTION

Other objects and advantages will be accomplished by the present invention which serves to warm a selected sympathetic center—or natural thermostat—of a human body, especially one of those proximate the hands and feet of a user, during sedentary activity. Moreover, in the preferred embodiment the body warming device may be used to warm the thermostats of a user's body proximate the hands during substantially any activity. A covering member is provided for covering a selected portion of a user's body. The covering member includes a shell member which defines an opening proximate one end and an interior volume configured to closely receive the selected portion of the body to be warmed.

A heat source receptacle is provided for receiving and retaining a heat source. The heat source receptacle includes at least one pocket defined within the shell member. The pocket defines an opening through which the heat source may be selectively introduced and removed. The heat source receptacle is dimensioned to closely receive the selected heat source such that migration of the heat source is minimized. The heat source receptacle is positioned such that the heat source, when received therein, is disposed proximate the natural thermostat within the selected body part to be warmed.

A closure member is provided for closing the heat source receptacle in order to prevent the unselected removal of the heat source. The closure member may include a flap member secured along one side to the covering member such that the flap will substantially cover the openings defined by the shell member and the heat source receptacle. The flap may be secured to the covering member on an opposing side in order to maintain the closing of the openings by means of a conventional closure member such as hook-and-loop type fasteners, snaps, and buttons. Other conventional closure member such as zippers may also be incorporated as well.

An insulation is provided for regulating the temperature within the covering member. The insulation serves to maintain the temperature within the covering member at approximately 140° F. In the preferred embodiment, a non-migratory insulation is used such that the insulation will remain evenly distributed over the area of the covering member. In order to maintain a comfortable temperature within the body warming device, the insulation is fabricated from a material which allows at least a limited passage of air. The insulation of the preferred embodiment is positioned between the shell member and the heat source receptacle pocket such that the heat source will be positioned between the selected portion of the body being warmed and the insulation.

A lining member may be incorporated to cover the insulation. The lining member is secured to the inner portion of the shell member about the respective perimeters by any conventional means such as sewing. An edging member may be provided for protecting the edges of the panel members, the lining, and the insulation.

A heat source is provided for generating heat within the inner volume of the covering member in order to replace the heat lost by the user's body at the selected location. The heat source recommended for use with the present invention is disposable and comprises naturally occurring materials which produce heat in reaction to the introduction of oxygen.

The body warming device may be configured to cover at least the toe of the footwear, with the heat source receptacle being positioned over the top portion of the foot, as this is the area of the local sympathetic center. It is envisioned that the present invention may be configured to additionally cover the heel portion of the foot, the top portion of the foot, or any other selected portion or portions of the foot as well. When the intended use is for covering a portion of the foot, the covering member includes a sole member and a top member. The sole member may be provided with a non-skid surface to prevent slipping along the support surface. A retaining strap may be provided for preventing the body warming device from unselected removal from the user's foot. In order to aid in the removal of the strap member, and likewise the body warming device, a tab member may be provided for easy engagement by the user's hand.

The body warming device may alternatively be configured for receiving at least one hand of a user, with the heat source receptacle being positioned over the back of the hand. Non-skid materials are not required when using the body warming device in conjunction with the warming of the hands. The embodiment described for use to warm the sympathetic centers of the foot may alternately be used to warm the users hand by securing the retaining strap to the wearer's clothing and allowing the body warming device to hang.

BRIEF DESCRIPTION OF THE DRAWINGS

The above-mentioned features of the invention will become more clearly understood from the following detailed description of the invention read together with the drawings in which.

BEST MODE FOR CARRYING OUT THE INVENTION

Figure 1:
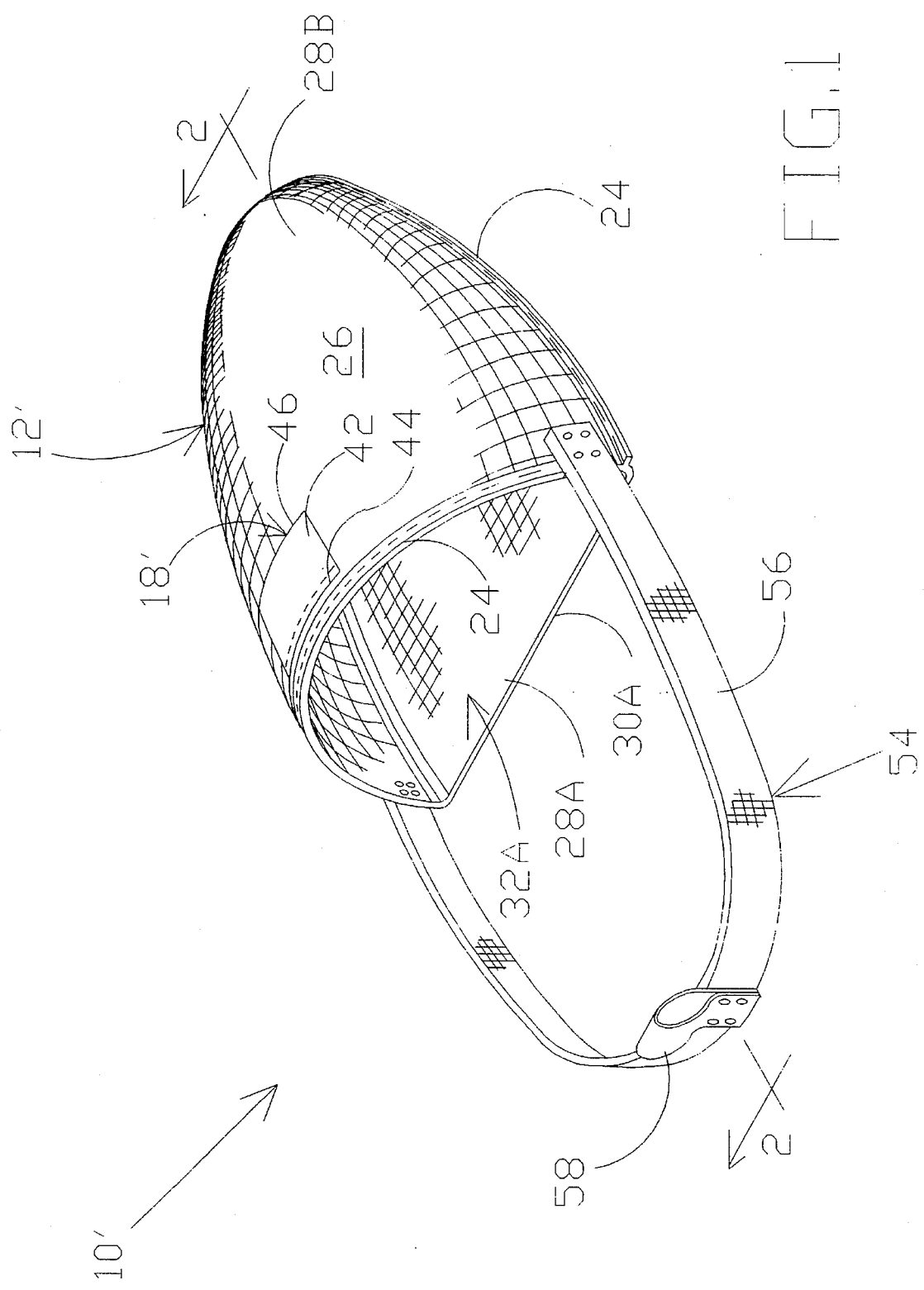
FIG. 1 is a perspective view of the body warming device constructed in accordance with several features of the present invention showing a configuration used to warm a user's foot.

A body warming device incorporating various features of the present invention is illustrated generally at 10 in the figures. The body warming device 10 is designed for warming the sympathetic centers 70—or natural thermostats—of a human body, such as located in the feet and hands of a user, during sedentary activity. Moreover, in the preferred embodiment the body warming device 10 may be used to warm the natural thermostats 70 located in various other parts of a user's body, such as the hands, during substantially any activity.

In the preferred embodiment, a covering member 12 is provided for covering a selected portion of a user's body. The covering member 12 includes a shell member 26 typically constructed of two panel members 28 fastened together about a substantial portion of their respective perimeters such as to define an opening 30 proximate one end and an interior volume 32. The interior volume 32 is configured to closely receive the selected portion of the body to be warmed. The interior volume 32 of the preferred embodiment is a unitary non-partitioned volume (i.e., no separate volumes are defined such as for the insertion of a wearer's thumb as would be provided in a conventional mitten, not shown). The interior volume 32 is defined by an interior perimeter which closely conforms to the perimeter of at least a portion of a user's hand and foot such that when the hand or foot is inserted into the interior volume 32, the interior volume 32 is substantially filled. In the preferred embodiment, the shell member 26 is manufactured from a water-repellant material such as acrylic. It will be seen that other conventional materials may be used to fabricate the shell member 26, and this disclosure is not intended to so limit the shell member 26 to an acrylic material.

A heat source receptacle 14 is provided for receiving and retaining a heat source 16. The heat source receptacle 14 of the preferred embodiment includes at least one pocket 36 defined within at least one of the panel members 28 which combine to form the shell member 26. The pocket 36 defines an opening 38 through which the heat source 16 may be selectively introduced and removed. The pocket opening 38 is dimensioned to cooperate with an opening 34 defined by the shell member 26 such that as the heat source 16 is introduced through the shell member opening 34, the heat source 16 is directly passed through the pocket opening 38 and into the interior volume 40 of the pocket 36.

The heat source receptacle 14 is dimensioned to closely receive the selected heat source 16 such that migration of the heat source 16 is minimized. The heat source receptacle 14 is positioned on the shell member 26 such that when the body warming device 10 is used the heat source 16 is disposed proximate a sympathetic center 70 of the human body. Therefore, the heat source 16 directly heats the air surrounding the sympathetic center 70 thereby preventing the loss of heat from the body. The heat source 16 also serves to heat the air within the body warming device 10 to further warm the selected portion of the body received within the body warming device 10.

The heat source receptacle 14 is fabricated from a material which is heat permeable, thereby allowing the heat generated by the heat source 16 to penetrate and enter the inner volume 32 of the covering member 12. Nylon has been used to fabricate the heat source receptacle 14. However, other selected materials may be used to attain the same results.

A closure member 18 is provided for closing the heat source receptacle 14 in order to prevent the unselected removal of the heat source 16 through the opening 38 defined by the pocket 36. As shown in the illustrations, the closure member 18 of the preferred embodiment includes a flap member 42 secured along one side 44 to the covering member 12 such that the flap member 42 will substantially cover the openings 34,38 defined by the shell member 26 and the heat source receptacle 14, respectively. The flap member 42 may be secured to the covering member 12 on an opposing side 46 in order to maintain the closing of the openings 34,38. A conventional closure member 18 may be used to accomplish the securement of the flap member 42 to the covering member 12. Such conventional closure member 18 includes, but is not limited to, hook-and-loop type fasteners 48, snaps, and buttons. It will be seen that the closure member 18 may include only a zipper (not shown) to selectively open and close the volume 40 within the heat source receptacle 14. Other conventional closure member 18 may be substituted as well.

An insulation 20 is provided for regulating the temperature within the inner volume 32 defined by the covering member 12. The insulation 20 serves to maintain the temperature within the covering member 12 at approximately 140° F. In the preferred embodiment, a non-migratory insulation is used such that the insulation 20 will remain evenly distributed over the area of the covering member 12. Non-migratory insulation is typically manufactured in sheet form. It will be seen that other temperatures may be attained as desired by varying the insulating material used.

In order to maintain a comfortable temperature within the body warming device 10, the insulation 20 is fabricated from a material which allows at least a limited passage of air. One preferred material from which the insulation 20 may be fabricated from is Thermalite®, manufactured by the 3-M Company. Other materials such as those produced by Gortex and Cordura may also be used. This disclosure is not intended to limit the insulation 20 to any of these materials, however.

As illustrated in the figures, the insulation 20 of the preferred embodiment is positioned between the shell member 26 and the heat source receptacle pocket 36. It will be seen, then, that the heat source 16, when placed, will be positioned between the selected portion of the body being warmed and the insulation 20. By so positioning the insulation 20, the heat generated by the heat source 16 will remain substantially within the body warming device 10.

As previously discussed, however, it is preferred that the insulation 20 have some degree of air permeability, or "breathing". Therefore, some heat will escape through the insulation 20, the amount of air escaping being determined by the qualities of the insulation material used. The escape of heat is necessary in order to prevent the interior 32 of the body warming device 10 from reaching a temperature which is too high.

Extremely high temperatures would result if a heat source 16 as used in the present invention was to be inserted into an existing shoe or boot. The temperature would reach levels such that discomfort, and possibly physical harm, could occur. Constant removal and replacement of the heat source would be required to avoid such problems, which in and of itself would create yet another problem.

A lining member 22 may be incorporated to cover the insulation 20. The lining member 22 of the preferred embodiment defines a substantially similar configuration as the panel members 28. The lining member 22 is secured to the panel members 28 about the respective perimeters by any conventional means such as sewing. An edging member 24 may be provided for protecting the edges of the panel members 28, the lining 22, and the insulation 20.

A heat source 16 is provided for generating heat within the inner volume 32 of the covering member 12 in order to replace the heat lost by the user's body at the selected location. The heat source 16 recommended for use with the present invention is disposable and comprises naturally occurring materials which produce heat in reaction to the introduction of oxygen. One available heat source 16 is the Hot Hands® manufactured by Heat Max Inc. in Dalton, Ga. This type of heat source 16 generates heat for up to 24 hours or longer and at levels sufficient to maintain the proper body temperature. Furthermore, this particular heat source 16 is environmentally safe, as all components are naturally occurring and the pouch within which the reacting materials are stored is biodegradable. Other heat sources are available and may be used with the present invention, and this disclosure is not intended to limit the heat source to this particular type.

Figure 2:
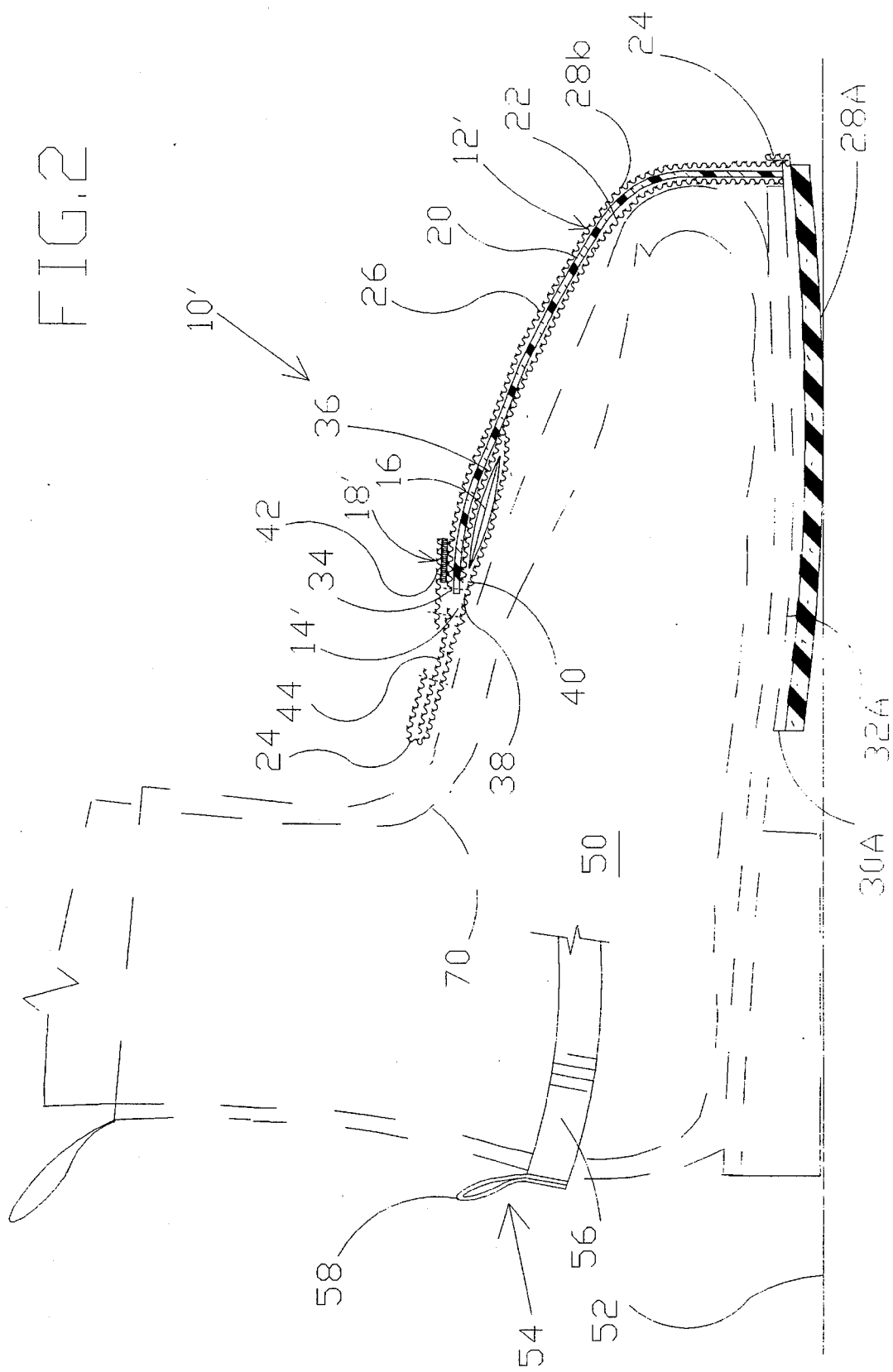
FIG. 2 illustrates a side elevation view, in section, of the body warming device taken at 2—2 of FIG. 1.

As shown in FIGS. 1 and 2, the body warming device 10' may be configured to cover at least the toe and upper portion of the top of the footwear 50. It is envisioned that the present invention may be configured to additionally cover the heel or any other selected portion or portions of the foot as well. In the illustrated embodiment, the covering member 12' includes a sole member 28A and a top member 28B connected such as to define an opening 30A at one end and a volume 32A within which the selected portion of the foot—i.e., the toe—and the associated portion of the footwear 50 is inserted. As depicted, the covering member 12' of this embodiment is dimensioned such that the user is not required to remove the footwear 50 in order to place the body warming device 10' in the selected position.

The sole member 28A is provided for engaging the support surface 52 upon which the user is standing or walking. Because the user will tend to walk at least limited distances, the sole member 28A may be provided with a non-skid surface to prevent slipping along the support surface 52.

The heat source receptacle 14' may be provided within the top member 28B, as shown most clearly in FIG. 2. Though the heat source receptacle 14' is illustrated in the top member 28B, it may very well be located in other selected locations on either the top member 28B or conceivably the sole member 28A. The heat source receptacle 14' of this embodiment is as disclosed previously.

In the embodiment of the body warming device 10' wherein the intended use is for warming the sympathetic center 70 of the foot, a retaining member 54 may be provided for preventing the body warming device 10' from unselected removal of the user's foot. To achieve this end, a strap member 56 may be provided. The strap member 56 of the preferred embodiment is fixed at either end to the covering member 12' at opposing sides of the opening 30A defined by the sole and top members 28A,28B. The strap member 56 is preferably fabricated from an elastomeric material such that the strap member 56 may be stretched to fit over the heel of a user, and then when placed, may be biased back toward the covering member 12', thereby further biasing the covering member 12', toward the user's foot.

In order to facilitate the removal of the strap member 56, and likewise the body warming device 10', a tab member 58 may be provided for easy engagement. It will be seen that the tab member 58 may be fabricated from any selected material.

Figure 3:
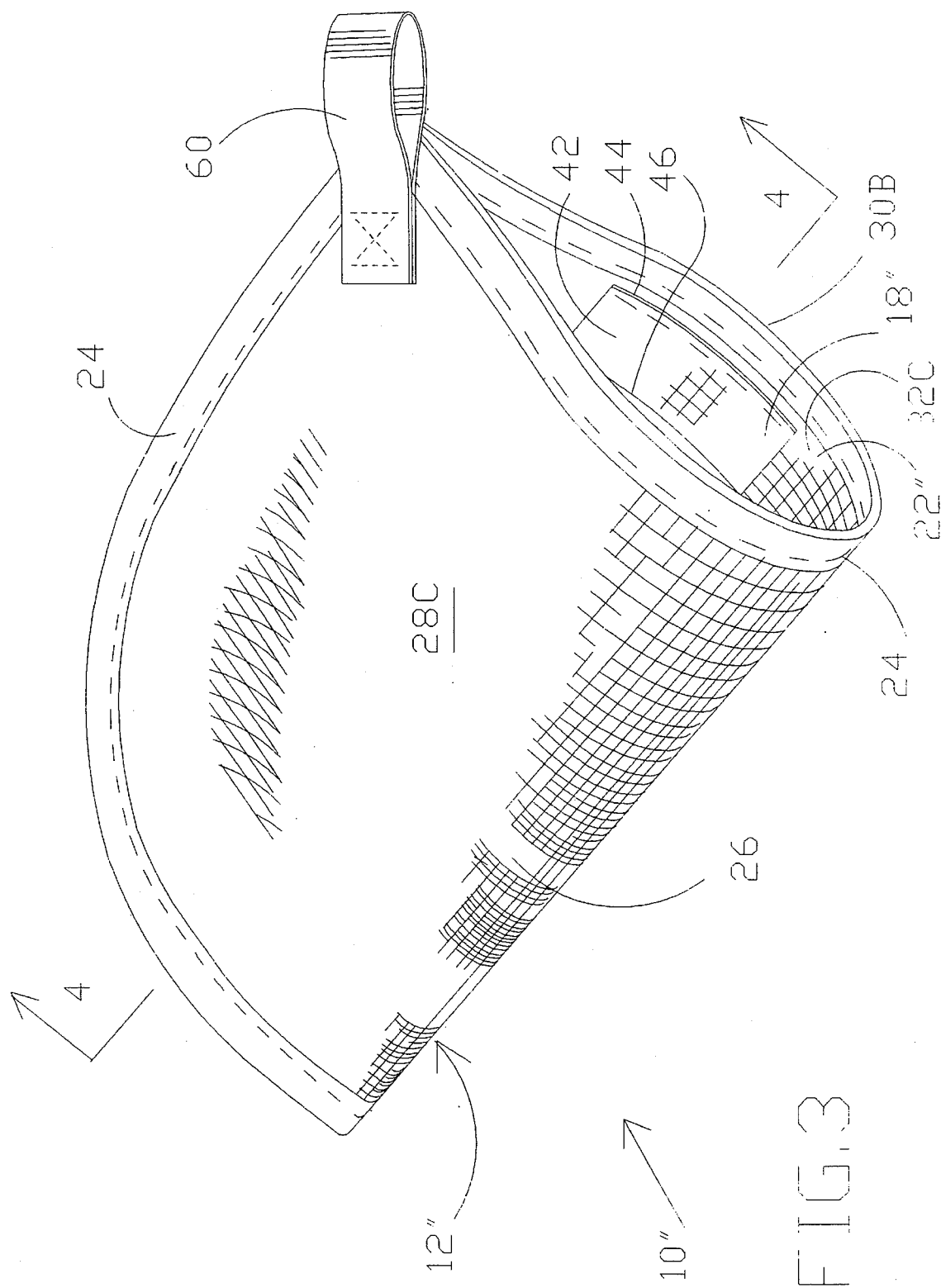
FIG. 3 is a perspective view of the body warming device constructed in accordance with several features of the present invention showing a configuration used to warm a user's hand.
Figure 4:
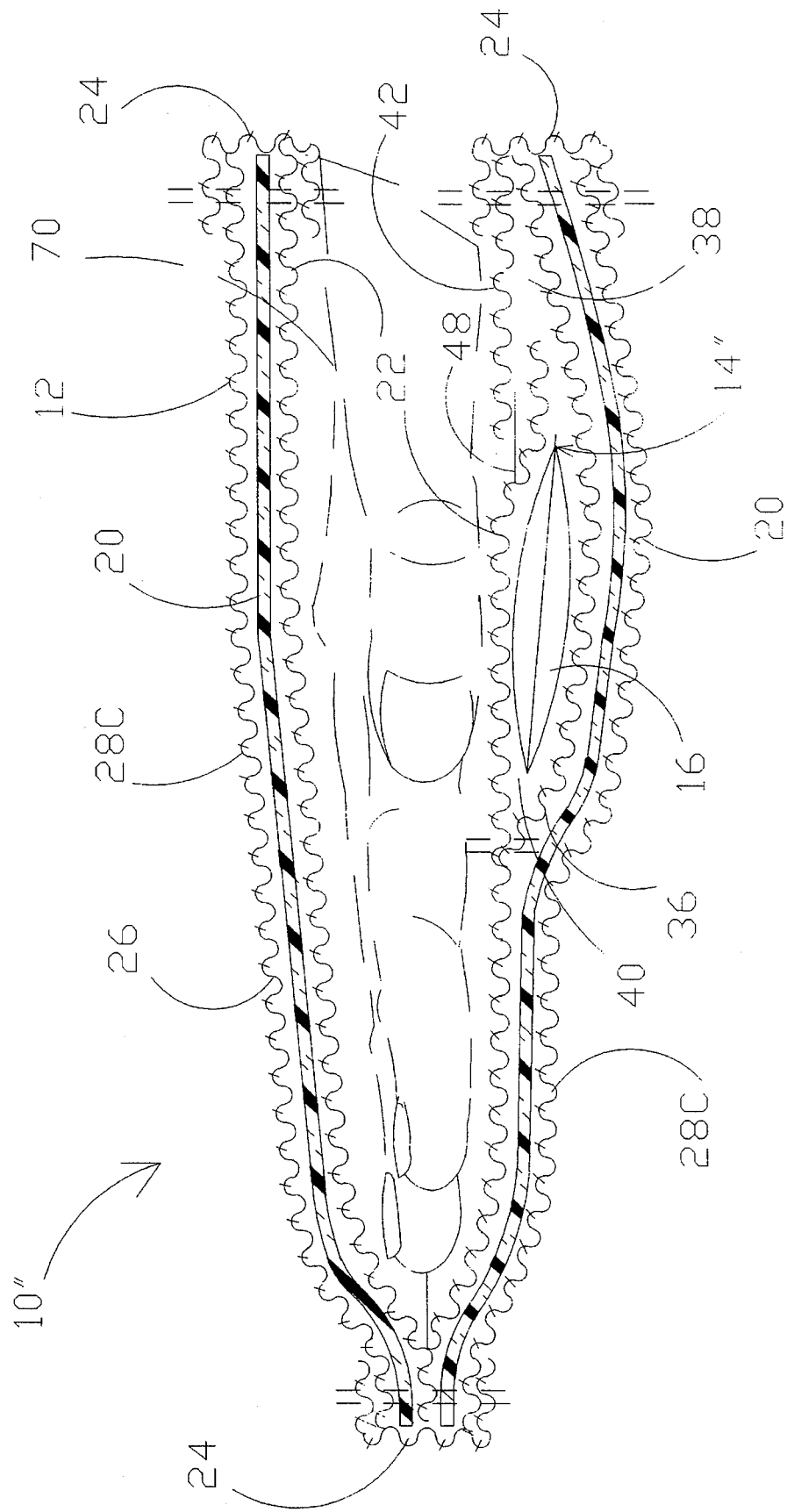
FIG. 4 illustrates a side elevation view, in section, of the body warming device taken at 4—4 of FIG. 3.

In the embodiment shown in FIGS. 3 and 4, the body warming device 10" may be configured for receiving at least one hand of a user. In this embodiment, it will be seen that the need for two panel members 28 is obviated. A single panel member 28C may be used and folded substantially in half, with the periphery sewn or otherwise fixed to define an opening 30B at one end for the entry of at least one of the user's hands.

In this embodiment, it will be seen that, as shown in the Figures, the heat source receptacle 14" may be positioned within the inner volume 32" of the covering member 12". It will be seen that non-skid materials are not required when using the body warming device 10" in conjunction with the warming of the hands.

A loop member 60 may be carried by the covering member 12" for receiving a belt (not shown) of a user such that the body warming device 10" may be carried by the belt of the user. When the body warming device 10" is so carried, the user may selectively place his hand within and withdraw his hand from the body warming device 10" without requiring the user to place the body warming device 10" where it may be lost. Further benefits may be recognized by securing the body warming device 10" to the belt of the user.

Other configurations of the present invention may be derived within the full scope and extent of the present disclosure. Two specific embodiments have been described and illustrated, but it is not the intent of the disclosure to limit the body warming device 10" to such configurations.

From the foregoing description, it will be recognized by those skilled in the art that a body warming device 10 offering advantages over the prior art has been provided. Specifically, the body warming device 10 provides a means for generating heat within a volume 32 into which a user's hand or foot is inserted. The body warming device may be used as a foot warmer, as in FIGS. 1 and 2, while it may further be used as a hand warmer, as in FIGS. 3 and 4. The body warming device 10, no matter which selected configuration is used, is designed to regulate the loss of heat to the atmosphere, the heat being produced by a heat source 16.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, I claim:

1. A body warming device for warming one of any of the extremities of a person's body proximate a sympathetic center located therein, said extremities including the hands and feet of said person's body, said body warming device being used in conjunction with a nonelectric heat source for elevating the temperature within said body warming device, said body warming device comprising:

a covering member defining an opening and a unitary, non-partitioned interior volume for the insertion of a portion of said selected extremity of said person's body, said unitary, non-partitioned interior volume defining an inside perimeter, the entire said inside perimeter closely conforming to a perimeter of said portion of said selected extremity such that said unitary, non-partitioned interior volume is substantially filled, said selected extremity including said sympathetic center, said covering member being capable of being selectively moved between a first selected position and a second selected position, said covering member being dimensioned to closely receive and encapsulate at least a portion of one of said feet of said person's body when engaged in said first selected position and to closely receive and encapsulate at least a portion of at least one of said hands of said person's body when engaged in said second selected position;

a heat source receptacle carried by said covering member for receiving said nonelectric heat source within a selected portion of said covering member, said heat source receptacle being positioned such that when said nonelectric heat source is received therein, said nonelectric heat source is positioned directly above said sympathetic center; said heat source receptacle being fabricated from a heat permeable material, said heat source receptacle including a pocket member defining an opening, said opening cooperating with an opening defined by said covering member to receive said nonelectric heat source, said pocket member being secured to said covering member proximate said covering member opening;

a closure member for preventing said nonelectric heat source from being unselectively removed from said heat source receptacle;

insulation for controlling said temperature within said body warming device;

a lining member for protecting said insulation, said lining member being configured to define a perimeter substantially similar to a perimeter defined by said covering member, said lining member being secured to said covering member about said perimeters defined by each of said lining member and said covering member, said insulation being disposed between said lining member and said covering member; and a securement member defining a continuous retainer strap fixed at opposite ends to said covering member proximate opposing sides of said opening, said retainer strap being dimensioned to selectively engage a heel portion of one of said feet of said person's body when said covering member is engaged in said first selected position, said retainer strap biasing said covering member toward said heel portion to prevent unselected removal of said body warming device, and said retainer strap further being dimensioned to selectively engage a selected garment worn on said person's body when said covering member is engaged in said second selected position.

2. The body warming device of claim 1 wherein said insulation is fabricated from a non-migratory material.

3. The body warming device of claim 1 wherein a portion of said insulation is position between said covering member and said heat source receptacle.

4. The body warming device of claim 1 wherein said covering member is fabricated from a water repellant material.

5. The body warming device of claim 1 wherein said insulation defines an opening proximate said opening of said covering member and said opening of said pocket member to cooperate with said covering member and said pocket member to facilitate said reception of said nonelectric heat source into said heat source receptacle.

6. A body warming device for warming one of any of the extremities of a person's body proximate a sympathetic center located therein, said extremities including the hands and feet of said person's body, said body warming device being used in conjunction with a nonelectric heat source for elevating the temperature within said body warming device, said body warming device comprising:

a covering member defining an opening and a unitary, non-partitioned interior volume for the insertion of a portion of said selected extremity of said person's body, said unitary, non-partitioned interior volume defining an inside perimeter, the entire said inside perimeter closely conforming to a perimeter of said portion of said selected extremity such that said unitary, non-partitioned interior volume is substantially filled, said selected extremity including said sympathetic center, said covering member being capable of being selectively moved between a first selected position and a second selected position, said covering member being dimensioned to closely receive and encapsulate at least a portion of one of said feet of said person's body when engaged in said first selected position and to closely receive and encapsulate at least a portion of at least one of said hands of said person's body when engaged in said second selected position, said covering member being fabricated from a water repellant material;

a heat source receptacle carried by said covering member for receiving said nonelectric heat source within a selected portion of said covering member, said heat source receptacle being positioned such that when said nonelectric heat source is received therein, said nonelectric heat source is positioned proximate said sympathetic center, said heat source receptacle being fabricated from a heat permeable material, said heat source receptacle including a pocket member defining an opening, said opening cooperating with an opening defined by said covering member to receive said nonelectric heat source, said pocket member being secured to said covering member proximate said covering member opening;

insulation for controlling said temperature within said body warming device, said insulation being fabricated from a non-migratory material, and being positioned between said covering member and said heat source receptacle, said insulation defining an opening proximate said opening of said covering member and said opening of said pocket member to cooperate with said covering member and said pocket member to facilitate said reception of said nonelectric heat source into said heat source receptacle;

a closure member for preventing said nonelectric heat source from being unselectively removed from said heat source receptacle;

a lining member for protecting said insulation, said lining member being configured to define a perimeter substantially similar to a perimeter defined by said covering member, said lining member being secured to said covering member about said perimeters defined by each of said lining member and said covering member, said insulation being positioned between said covering member and said lining member; and a securement member defining a continuous retainer strap fixed at opposite ends to said covering member proximate opposing sides of said opening, said retainer strap being dimensioned to selectively engage a heel portion of one of said feet of said person's body when said covering member is engaged in said first selected position, said retainer strap biasing said covering member toward said heel portion to prevent unselected removal of said body warming device, and said retainer strap further being dimensioned to selectively engage a selected garment worn on said person's body when said covering member is engaged in said second selected position.

7. The body warming device of claim 6 wherein said covering member includes a sole member for engaging a bottom portion of one of said feet of said person's body and a top member.

8. The body warming device of claim 7 wherein said sole member is provided with a non-skid surface to prevent slippage of said one of said feet of said person's body along a support surface.

9. The body warming device of claim 6 further comprising an engagement member secured to said retainer strap, said engagement member being configured to be selectively engaged by a person for selective placement and removal of said body warming device.

10. The body warming device of claim 6 wherein said covering member is configured to closely receive at least a selected portion of one of said hands of said person's body.

* * * * *